United States Patent
Guillet

[11] Patent Number: 6,050,991
[45] Date of Patent: Apr. 18, 2000

[54] PULSED-EMISSION LASER FOR USE IN THE MEDICAL FIELD

[75] Inventor: Hubert Gaston Guillet, Vienne, France

[73] Assignee: LOKKI S.A. (SociétéAnonyme), Vienne, France

[21] Appl. No.: 08/809,360

[22] PCT Filed: Sep. 28, 1995

[86] PCT No.: PCT/FR95/01258

§ 371 Date: Mar. 28, 1997

§ 102(e) Date: Mar. 28, 1997

[87] PCT Pub. No.: WO96/09799

PCT Pub. Date: Apr. 4, 1996

[30] Foreign Application Priority Data

Sep. 29, 1994 [FR] France ................................. 94-11865

[51] Int. Cl.[7] ................................................. A61B 17/36
[52] U.S. Cl. ................................................. 606/10; 607/89
[58] Field of Search ................................. 606/3, 10, 15, 606/16

[56] References Cited

U.S. PATENT DOCUMENTS

| | | | |
|---|---|---|---|
| 4,039,970 | 8/1977 | Shiroki | 331/94.5 |
| 5,130,997 | 7/1992 | Ortiz | 372/21 |
| 5,180,378 | 1/1993 | Kung | 606/10 |
| 5,304,167 | 4/1994 | Freiberg | 606/3 |
| 5,456,603 | 10/1995 | Kowalzk | 433/215 |

OTHER PUBLICATIONS

Hanson, "Laser–diode Side–pumped Nd:YAlO3 Laser at 1.08 and 1.34 mu. m", 2412 Optics Letters, Optical Soc. of America, Jul. 1989.

*Primary Examiner*—Linda C. M. Dvorak
*Assistant Examiner*—Roy Gibson
*Attorney, Agent, or Firm*—Bacon & Thomas

[57] ABSTRACT

A method of ablating or cutting tissue with a laser depending upon whether the tissue is hard or soft, including the steps of aiming a laser favoring emission of light radiation at a wavelength of 1.34 $\mu$m at the tissue, ablating the tissue with the laser when the tissue is hard tissue, and cutting the tissue with the laser when the tissue is soft tissue.

8 Claims, 1 Drawing Sheet

PULSED-EMISSION LASER FOR USE IN THE MEDICAL FIELD

BACKGROUND OF THE INVENTION

1. Field of the Invention

The present invention relates to the technical field of devices designed to emit pulsed laser beams for use in the medical field in a broad sense.

In the medical field, lasers are used mainly either for incision or cutting purposes analogous to a scalpel, or else for coagulating or cauterizing human tissue.

2. Description of Related Art

Thus, it is known to make use of a neodymium-doped Nd YAG laser at a wavelength of 1.06 $\mu$m. The light radiation is absorbed by tissue and enables the tissue to be heated, and the associated cauterizing effect to be obtained. At this wavelength, the laser beam is transmitted by a silica optical fiber which enables it to be used inside the body without requiring a surgical opening. Pulsed operation makes it possible to drill and abrade hard tissue. Nevertheless, cutting soft tissue is lengthy and the cut is broad, with too deep a zone being affected thermally.

It is also known to use a $CO_2$ laser beam which enables tissue to be vaporized, such that the focused beam cuts into the surface and makes an incision. Such a beam which operates at a wavelength of about 10 $\mu$m is highly absorbed by tissue. Soft tissue is cut well. However, hard tissue is sometimes cracked by thermo-diffusion of the laser. Also, the $CO_2$ laser beam does not propagate along flexible optical fibers, so the beam needs to be fed by means of a relatively complex combination of tubes and mirrors.

In order to combine the advantages of both of the above lasers, proposals have been made to implement a device integrating two lasers of the above types. Nevertheless, it must be understood that the $CO_2$ laser retains its drawbacks, thereby considerably restricting the field in which such a device can be applied.

French patent application FR 2 607 329 proposes an Nd YAG laser fitted with beam wavelength selection means for selecting a value of 1.44 $\mu$m. At that wavelength, light is better absorbed by the water contained in tissue than is light at a shorter wavelength, e.g. equal to 1.32 $\mu$m or to 1.06 $\mu$m, which are the other transition values of an Nd YAG laser.

When a powerful laser beam at the wavelength of 1.44 $\mu$m is focused on tissue, the surface of the tissue is heated and evaporates in a manner that is substantially identical to using a $CO_2$ laser beam, thus providing an incision in the tissue. The major drawback of that laser device lies in its low efficiency, requiring the use of overdimensioned excitation and cooling means in order to obtain laser power that is sufficient for most of the intended applications. The resulting prohibitive cost has restricted the spread of that laser device.

The Applicant has examined numerous prior art solutions and has thus found that there does not exist any multipurpose lasers providing a beam that can be transmitted by optical fibers.

The Applicant thus has the merit of drawing up a list of characteristics that ought to be found in a laser device for medical use, in order to satisfy user needs. It has thus been observed that the laser beam needs to possess a wavelength that is suitable for being absorbed both by hard tissue and by soft tissue, so as to make it possible both to cut and coagulate soft tissue and to remove hard tissue. The term "soft tissue" is used, for example, to cover mucous membranes, gums, dental pulp, parenchyma, muscles, or tumors, while the term "hard tissue" is used to cover, for example, enamel, dentine, calculi, bone, cartilage, or atherosclerosis.

Additionally, a laser beam at such a wavelength must be capable of propagating along a flexible optical fiber so as to be suitable for inserting inside hollow organs, and more generally, the human or animal body. Also, such a device should be compact and easy to use.

In numerous applications, a laser device must deliver power in the range 2 watts to 20 watts. To deliver such power, a laser device must have good efficiency so as to avoid using excitation means and consequently cooling means that are too powerful, which increases in prohibitive manner both the size and the cost of manufacturing such a laser, thus making it inaccessible in numerous applications.

The Applicant has thus shown that there exists a need for a laser device capable of cutting soft tissue and of ablating hard tissue, providing a beam that is suitable for being conveyed by means of a flexible optical fiber, and that is of an efficiency that is suitable for enabling it to be implemented at an acceptable cost in the numerous uses for which the device is intended.

After specifying the above need, the Applicant has developed a laser device that satisfies the set of technical characteristics required in the various applications envisaged.

SUMMARY OF THE INVENTION

The invention thus relates to a device providing pulsed laser beam emission, the device being of the type comprising:

a laser rod;

excitation means for pulsed excitation of the laser rod to cause it to deliver light radiation;

a resonator placed on either side of the rod and enabling laser light radiation to be emitted; and selection means for selecting the wavelength of the emitted laser light radiation.

According to the invention, the laser rod is a neodymium-doped crystal of yttrium aluminum perovskite, known by the initials YAP, or of yttrium aluminum lanthanate, known by the initials YALO or $YALO_3$, and the selection means are designed to favor emission of light radiation at a wavelength of 1.34 $\mu$m, so as to ensure a thermal effect both on soft tissue and on hard tissue.

Various other characteristics appear from the following description given with reference to the accompanying drawings which show embodiments and implementations of the invention as non-limiting examples.

DETAILED DESCRIPTION OF THE PREFERRED EMBODIMENT

Figure 1:
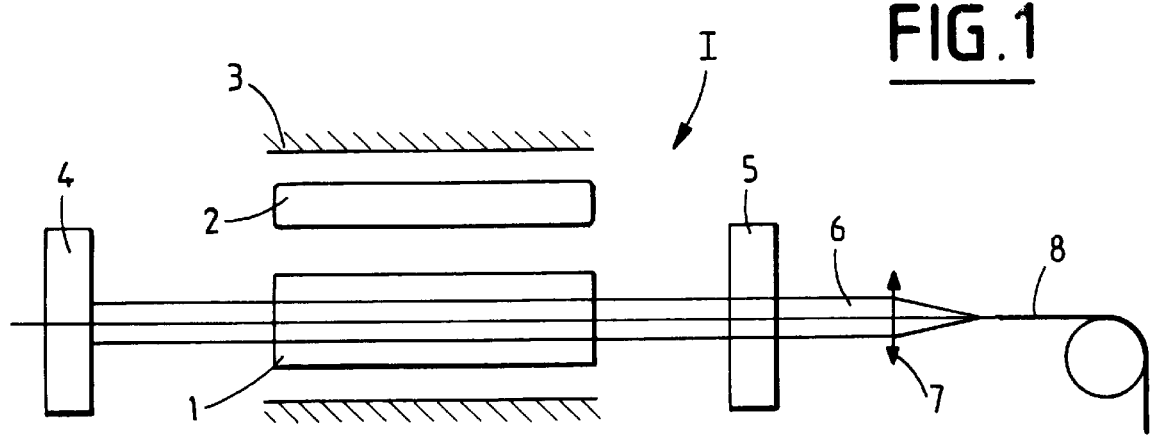
FIG. 1 is a diagrammatic view of an embodiment of a laser device of the invention.

As can be seen more precisely in FIG. 1, the laser device I of the invention comprises an active medium or laser rod 1 which is advantageously constituted by a crystal of yttrium aluminum perovskite, referred by the initials YAP, and sometimes also known as YALO or $YALO_3$ for yttrium aluminum lanthanate. Such a crystal is doped with neodymium in a percentage range of 0.4 to 2, and preferably substantially about 0.8%. A laser rod of YAP, YALO, or YALO$_3$ normally radiates at wavelengths equal to 1.07 μm or 1.34 μm.

The laser rod 1 is associated with excitation means including an excitation lamp 2 connected to a pulsed lamp excitation circuit (not shown), and a reflecting envelope 3 in which both the excitation lamp 2 and the rod 1 are mounted. The duration of excitation, which is achieved by any appropriate means known per se, lies in the range 10 μs to 10 ms. For example, the excitation lamp 2 may be constituted by laser diodes or by a xenon or krypton discharge lamp. Advantageously, it is a xenon lamp and its envelope is adapted to eliminate or filter ultra-violet radiation from the lamp at a wavelength shorter than 350 nm. The reflecting envelope 3 preferably filters or eliminates ultraviolet radiation at a wave-length shorter than 350 nm. Naturally, any other means may be envisaged for implementing filtering of the light radiation. For example, a filter may be interposed between the lamp 2 and the rod 1. Implementing such filter means, on their own or in combination, serves to avoid the appearance of the crystal solarization phenomenon.

The laser device I also includes a resonator 4, 5 enabling a laser light beam 6 to be emitted. The resonator comprises two mirrors 4 and 5 disposed at opposite ends of the laser rod 1. Advantageously, the resonator 4, 5 is designed to select the wavelength of the light radiation emitted by the rod 1 so as to favor emission at the wavelength of 1.34 μm. The mirrors 4 and 5 thus have reflection coefficients that are optimized to favor emission at 1.34 μm and to prevent emission at 1.07 μm. For example, the mirror 4 may have a reflection maximum at 1.35 μm, while the other mirror 5 is 20% to 80% reflective at 1.34 μm and is antireflective at 1.07 μm. In this manner, the laser operates in "relaxed" free emission with pulses of duration close, i.e, substantially equal to the excitation duration, and all of the laser energy is emitted at the wavelength of 1.34 μm.

The laser beam 6 is focused by means of a lens 7 on the inlet of an optical fiber 8 which conveys it to the tissue to be treated. The optical fiber has a silica core which is preferably made of so-called "dry" silica having low OH ion content.

The laser device I of the invention thus has the special feature of operating at a wavelength of 1.34 μm, at which wavelength tissue absorbs light radiation well. It is thus possible to cut soft tissue with results comparable to those obtained with a continuous $CO_2$ laser, but with additional advantages such as less smoke, better hemostasis and coagulation, and better accessibility due to the optical fiber. It also turns out that such a laser device ablates hard tissue with a result equivalent to a pulsed Nd YAG laser. The laser device I is thus suitable for exerting thermal effects on biological tissue such as cutting, coagulation, and vaporization of soft tissue or drilling, abrasion, and melting of hard tissue.

Figure 2:
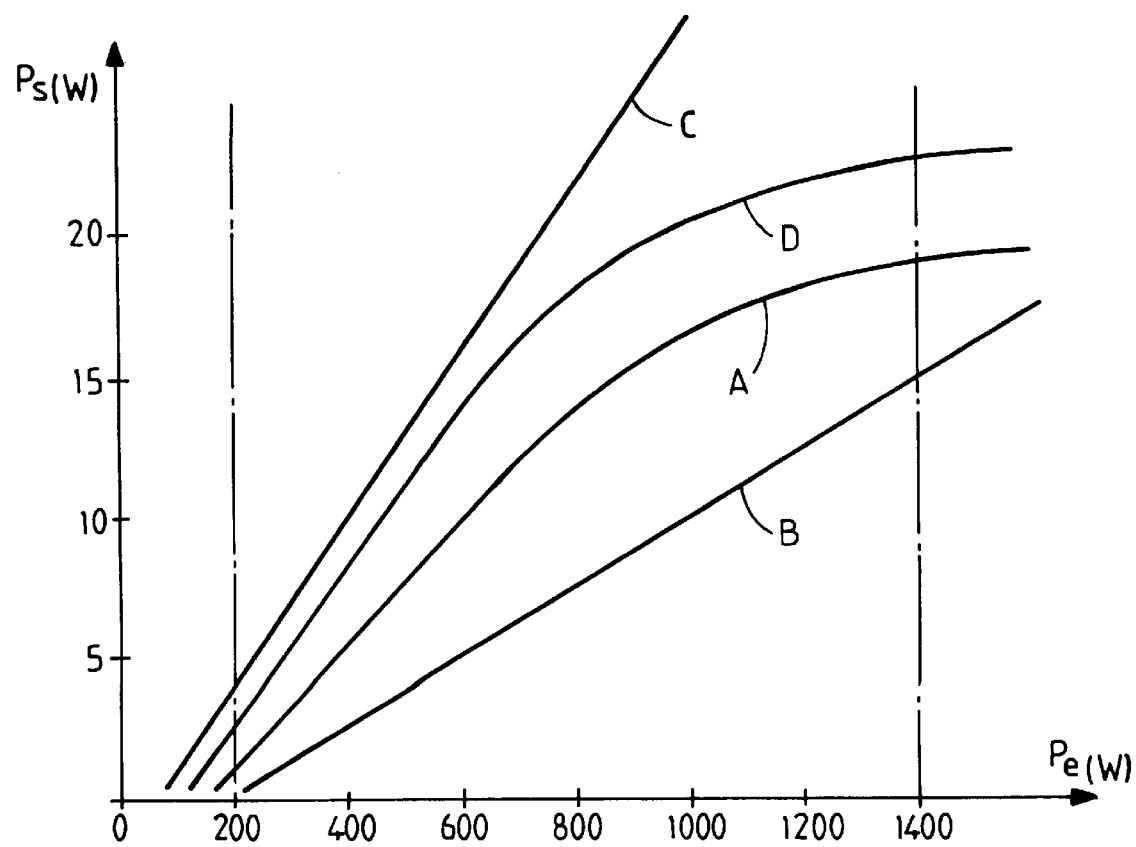
FIG. 2 is a diagram showing the power characteristics of various lasers as a function of the associated pumping power.

The laser of the invention has another advantage, namely relatively high efficiency compared with known lasers. This advantage is shown in FIG. 2 which plots the laser power characteristics Ps as a function of pumping power Pe for various types of laser placed in similar pumping configurations. For pumping power values lying substantially in the range 200 watts to 1,400 watts, the laser power (curve A) obtained with the laser device of the invention at the wavelength of about 1.34 μm is greater than that (curve B) of an Nd YAG laser at 1.32 μm. In practice, the expected efficiency is greater than 1%, and preferably about 2%, and such values cannot be obtained by a YAG laser at 1.32 μm (curve B). Even though the efficiencies obtained with an Nd YAG laser at 1.06 μm (curve C) or with an Nd YAP laser at 1.07 μm (curve D) are greater than those obtained with a laser of the invention operating at 1.34 μm, it must be understood that those two wavelengths (1.06 and 1.07) are insufficiently absorbed by tissue to ensure the desired thermal effects. The device I of the invention thus has good efficiency, for laser powers lying in the range 2 watts to 20 watts, and it provides light radiation at a wavelength which is, additionally, well absorbed so as to be able to perform the functions of cauterizing and cutting tissue.

POSSIBILITY OF INDUSTRIAL APPLICATION

The subject matter of the invention finds a particularly advantageous application in the field of dentistry, in particular for performing surgical operations, treatments at the bottoms of cavities, or treatments of canals. The laser device of the invention finds other applications in the medical field, in particular in orthopedics (percutaneous nucleotomy, meniscectomy), in neurosurgery, in gynecology (coelioscopic surgery), or in ENT (ear-nose-throat).

I claim:

1. A method of ablating or cutting tissue with a laser depending upon whether the tissue is hard or soft, comprising the steps of:

aiming a laser favoring emission of light radiation at a wavelength of 1.34 μm at the tissue;

ablating the tissue with the laser when the tissue is hard tissue; and cutting the tissue with the laser when the tissue is soft tissue.

2. The method as recited in claim 1, further comprising the steps of:

pulsing the laser with a duration of excitation in the range of 10 μs to 10 ms.

3. The method as recited in claim 1, wherein said laser includes a laser rod having a neodymium-doped crystal of yttrium aluminum perovskite.

4. The method as recited in claim 1, further comprising:

pulsing the laser in relaxed free emission with pulses of duration substantially equal to an excitation duration of the laser.

5. The method as recited in claim 1, wherein said aiming step further includes conveying said light radiation to the tissue with an optical fiber.

6. A method of ablating or cutting tissue depending upon whether the tissue is hard or soft, comprising the steps of:

aiming a laser including a laser rod having a neodymium-doped crystal of yttrium aluminum perovskite favoring emission of light radiation at a wavelength of 1.34 μm at the tissue;

pulsing the laser in relaxed free emission with pulses of duration substantially equal to an excitation duration of the laser;

ablating the tissue with the laser when the tissue is hard tissue; and cutting the tissue with the laser when tissue is soft tissue.

7. The method recited in claim 6, further comprising the steps of:

pulsing the laser with a duration of excitation in the range of 10 μs to 10 ms.

8. The method recited in claims 7, further comprising:

conveying said light radiation to the tissue with an optical fiber.

* * * * *